United States Patent [19]

Wiley

[11] 4,329,450
[45] May 11, 1982

[54] NOGALAMYCIN ANALOG CONTAINING COMPOUNDS

[75] Inventor: Paul F. Wiley, Portage, Mich.

[73] Assignee: The Upjohn Company, Kalamazoo, Mich.

[21] Appl. No.: 238,262

[22] Filed: Feb. 25, 1981

[51] Int. Cl.³ .................... A61K 31/71; C07H 15/24
[52] U.S. Cl. .................................. 536/6.4; 424/180; 536/119
[58] Field of Search .............................. 536/17 A, 119

[56] References Cited

U.S. PATENT DOCUMENTS

| | | | |
|---|---|---|---|
| 3,183,157 | 5/1965 | Bhuyan et al. | 536/17 A |
| 3,501,569 | 3/1970 | Wiley et al. | 536/17 A |
| 4,035,566 | 7/1977 | Israel et al. | 536/17 A |
| 4,064,340 | 12/1977 | Wiley et al. | 536/17 A |
| 4,064,341 | 12/1977 | Wiley et al. | 536/17 A |
| 4,086,245 | 4/1978 | Wiley et al. | 536/17 A |
| 4,183,860 | 1/1980 | Wiley et al. | 536/17 A |

*Primary Examiner*—Johnnie R. Brown
*Attorney, Agent, or Firm*—Roman Saliwanchik

[57] ABSTRACT

Novel regioselective acylates of the antibiotic nogalamycin and its dimethylamino-retaining analogs are prepared by a selective acylation procedure. The compounds of the invention have antibacterial activity, and, thus, can be used in various environments to control or eradicate susceptible bacteria.

7 Claims, No Drawings

NOGALAMYCIN ANALOG CONTAINING COMPOUNDS

BACKGROUND OF THE INVENTION

The known antibiotic nogalamycin, and a process for its preparation, are described in U.S. Pat. No. 3,183,157. The structure of nogalamycin is shown in Chart I as compound I.

Antibiotics nogalarol and nogalarene, produced by acid hydrolysis of nogalamycin, and o-methylnogalarol, produced by acidic methanolysis of nogalamycin or nogalarol, are disclosed in U.S. Pat. No. 3,501,569.

Other analogs of nogalamycin are as follows:

| U.S. Pat. No. 4,064,340 | nogamycin |
| U.S. Pat. No. 4,064,341 | nogalamycinic acid |
| U.S. Pat. No. 4,086,245 | 7-con-O—alkylnogarols |
| U.S. Pat. No. 4,183,860 | 7-dis-O—alkylnogarols. |

All of the above nogalamycin analogs retain the dimethylamino moiety. Acylates of all the above compounds are disclosed as being made by "standard acylating" procedures which are non-selective as to hydroxyl groups being acylated.

BRIEF SUMMARY OF THE INVENTION

Regioselective acylates of nogalamycin, and its analogs which retain the dimethylamino moiety, are prepared by the invention process. This process selectively acylates the 2',4' hydroxyls to give compounds possessing antibacterial activity. For example, 2',4'-di-O-acetylnogamycin, prepared by the invention process, is active against *Bacillus subtilis*, and, thus, it can be used for treating breeding places of silkworms to prevent or minimize infections which are well known to be caused by this bacterium. It, and the other acylates, also can be used to minimize or prevent odor in fish and fish crates caused by contamination with B. subtilis. The compounds of the invention also can be used to treat birds infected with *Mycobacterium avium*. Generally, the novel regioselective acylates of this invention can be used for the same biological purposes as the parent unacylated compound is used.

DETAILED DESCRIPTION OF THE INVENTION

The regioselective acylates of the invention are at the 2',4' positions of a molecule which retains the dimethylamino moiety as shown in Chart I. The partial structure of these compounds can be shown as compound II in Chart I. The remainder of the structure can be that of nogalamycin or any of its dimethylamino-containing analogs. Exemplification of such analogs was given above under the BACKGROUND OF THE INVENTION.

The novel compounds of the invention can be prepared by suspending the starting nogalamycin compound in methanol and then adding the acid anhydride acylating agent. The mixture is allowed to stand at room temperature for from 2-6 hours. Thereafter, the reaction mixture can be evaporated to dryness in vacuo, and the residue chromatographed on silica gel. A suitable solvent system, for example, chloroformacetone (85:15) can be used as an eluent after which fractions are collected and the desired product recovered by standard techniques.

The subject process differs from the standard acylating process in that here the acid anhydride is suspended in methanol, whereas, in the standard procedure, the acylation with an acid halide or anhydride is carried out in the presence of acid-binding agents such as pyridine and sodium acetate.

Carboxylic acids suitable for acylation include (a) saturated or unsaturated, straight or branched chain aliphatic carboxylic acids, for example, acetic, propionic, butyric, isobutyric, tertbutylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like, (d) aromatic carboxylic acids, for example, benzoic acid, toluic acid, naphthoic acid, ethylbenzoic acid, isobutylbenzoic acid, methylbutylbenzoic acid, and the like; and (e) aromatic aliphatic carboxylic acids, for example, phenylacetic acid, phenylpropionic acid, phenylvaleric acid, cinnamic acid, phenylpropiolic acid, and naphthylacetic acid, and the like. Also, suitable halo-, nitro-, amino-, cyano-, and lower alkoxy- hydrocarbon carboxylic acids include hydrocarboncarboxlic acids as given above which are substituted by one or more of halogen, nitro, amino, cyano, or lower alkoxy, advantageously lower alkoxy of not more than six carbon atoms, for example, methoxy, ethoxy, propoxy, butoxy, amyloxy, hexyloxy groups and isomeric forms thereof. Examples of such substituted hydrocarbon carboxylic acids are:

mono-, di- and trichloroacetic acid;
α- and β-chloropropionic acid;
α- and γ-bromobutyric acid;
α- and δ-iodovaleric acid;
mevalonic acid;
2- and 4-chlorocyclohexanecarboxylic acid;
shikimic acid;
2-nitro-1-methyl-cyclobutanecarboxylic acid;
1,2,3,4,5,6-hexachlorocyclohexanecarboxylic acid;
3-bromo-2-methylcylcohexanecarboxylic acid;
4- and 5-bromo-2-methylcyclohexanecarboxylic acid;
5- and 6-bromo-2-methylcyclohexanecarboxylic acid;
2,3-dibromo-2-methylcyclohexanecarboxylic acid;
2,5-dibromo-2-methylcyclohexanecarboxylic acid;
4,5-dibromo-2-methylcyclohexanecarboxylic acid;
5,6-dibromo-2-methylcyclohexanecarboxylic acid;
3-bromo-3-methylcyclohexanecarboxylic acid;
6-bromo-3-methylcycloheanecarboxylic acid;
1,6-dibromo-3-methylcyclohexanecarboxylic acid;
2-bromo-4-methylcyclohexanecarboxylic acid;
1,2-dibromo-4-methylcyclohexanecarboxylic acid;
3-bromo-2,2,3-trimethylcyclopentanecarboxylic acid;
1-bromo-3,5-dimethylcyclohexanecarboxylic acid;
homogentistic acid, o-, m-, and p-chlorobenzoic acid;
anisic acid;
veratric acid;
trimethoxybenzoic acid;
trimethoxycinnamic acid;

4,4'-dichlorobenzilic acid;
o-, m-, and p-nitrobenzoic acid;
cyanoacetic acid;
3,4- and 3,5-dinitrobenzoic acid;
2,4,6-trinitrobenzoic acid;
cyanopropionic acid;
ethoxyformic acid (ethylhydrogencarbonate);
and the like.

Biologically acceptable acid addition salts of the 2',4' di-O-acylates of the subject invention can be made by neutralizing the acylate with an appropriate acid to below about pH 7.0, and advantageously to about pH 2 to pH 6. Suitable acids for this purpose include tartaric, glucuronic, and lactic which give water soluble salts, and hydrochloric, sulfuric, phosphoric, sulfamic, hydrobromic, and the like which give relatively water insoluble salts. Acid salts can be used for the same biological purposes as the parent acylate compound.

The following examples are illustrative of the process and products of the invention, but are not to be construed as limiting. All percentages are by weight and all solvent mixture proportions are by volume unless otherwise noted.

EXAMPLE 1

2',4'-Di-O-Acetylnogalamycin

One gram of nogalamycin, prepared as described in U.S. Pat. No. 3,183,157, is suspended in 15 ml. of methanol, and 3 ml of acetic anhydride is added. The mixture is allowed to stand at room temperature for 4 hours although solution occurs in only a few minutes. The reaction mixture is evaporated to dryness in vacuo, and the residue is chromatographed on 100 g of silica gel eluting with chloroform-acetone (85:15) and collecting 236 five-ml fractions. Fractions 125-183 are combined on the basis of tlc in chloroformacetone (4:1; $R_f$ 0.28). Evaporation in vacuo gave 753 mg of 2',4'-di-O-acetylnogalamycin homogeneous on the basis of tlc: $[\alpha]_D$ +416° (C 0.217, CHCl$_3$); UV (C$_2$H$_5$OH) 235 nm ($\epsilon$ 70,200), 257 (29,600), 288sh (13,080), 473 (28,100); IR (Nujol) 3460, 1750, 1675, 1620, 1570, 1380, 1295, 1220, 1145, 1100, 1035, 760 cm$^{-1}$; $^1$H NMR (CDCl$_3$) $\delta$ 1.17 (s, 3H, CH$_3$C), 1.27 (d, 3H, J=6.0 Hz, CH$_3$C), 1.46 (s, 3H, CH$_3$C), 1.62 (s, 3H, CH$_3$C), 2.15 (s, 3H, CH$_3$CO), 2.17 (s, 3H, CH$_3$CO), 2.28 [s, 6H, (CH$_3$)$_2$N], 2.67 (d of d, 1H, J=11 Hz, 10 Hz, H-3'), 3.11 (d, 1H, J=9.5 Hz, H-4"), 3.20, 3.52, 3.54, 3.78 (4s, 12H, CH$_3$O), 3.26 (d, 1H, J=1 Hz, H-2"), 3.70 (m, 1H, H-5"), 3.98 (s, 1H, H-10), 5.06-5.26 (m, 3H, H-2", H-4', and H-7), 5.41 (broad s, 1H, J=ca. 1 Hz, H-1"), 5.87 (d, 1H, J=3.5 Hz, H-1'), 7.04 (s, 1H, H-3), 7.59 (s, 1H, H-11), 12.28 and 12.67 (2s, 2H, phenolic OH); $^{13}$C NMR (CDCl$_3$) $\delta$ 182.3 (C-5), 179.6 (C-12), 172.0 (COOCH$_3$), 170.0, 169.4 (2 CH$_3$CO), 161.8 (C-6), 156.3 (C-4), 146.3 (C-1), 143.2 (C-10a), 135.9 (C-2), 134.0 (C-11a), 130.6 (C-6a), 123.9 (C-3), 120.0 (C-11), 117.2 (C-12a), 115.4 (C-4a), 114.5 (C-5a), 100.7 (C-1"), 92.7 (C-1'), 84.5 (C-4"), 81.2 (C-2"), 77.9 (C-3"), 74.0 (C-5'), 72.6, 72.3 (C-2' and C-4'), 70.1 (C-7), 69.8 (C-9), 67.4 (C-5"), 62.4 (C-3'), 61.3, 58.5, 48.6 (CH$_3$O at C-2", C-3", and C-4"); 56.8 (C-10), 52.6 (COOCH$_3$), 41.2 [(CH$_3$)$_2$N], 40.6 (C-8), 29.0 (C-9 CH$_3$), 22.4 (C-5' CH$_3$), 21.2, 21.0 (2CH$_3$CO), 18.2 (C-5" CH$_3$), 14.9 (C-3" CH$_3$); mass spectrum, m/e 871.

Anal. Calcd for C$_{43}$H$_{53}$NO$_{18}$: C, 59.23; H, 6.01; N, 1.61. Found: C, 57.33; H, 5.89, N, 1.35.

EXAMPLE 2

2',4'-Di-O-Acetyldisnogamycin

A mixture of 3 g of disnogamycin, prepared as described in U.S. Pat. No. 4,064,340, 9 ml of acetic anhydride and 45 ml of methanol is stirred for 5 hours. Solution occurs rapidly and then a precipitate begins to form. Filtration gives 1.20 g. This is combined with 400 mg of similar material and recrystallized from methanol, yield 690 mg, m.p. 247°-251° of 2',4'-di-O-acetyldisnogamycin.

The first filtrate is evaporated to dryness in vacuo to give 2.04 g which is combined with 1.02 g of similar material. The resulting material is chromatographed on 30 g of silica gel eluting with chloroform-acetone (97:3). A total of 366 20-ml fractions are collected, and fractions 206-366 are combined on the basis of tlc in chloroform-methanol-water (78:20:2). The combined fractions are evaporated in vacuo to give 150 mg 2',4'-di-O-acetyldisnogamycin homogeneous by tlc in the above solvent system. A sample is recrystallized from methanol for analysis; $R_f$ 0.63 (CHCl$_3$-CH$_3$OH; 9:1), $[\alpha]_D$ +382° (C 0.9695, CHCl$_3$); UV (EtOH) 235 nm ($\epsilon$ 50,500), 254 (23,000), 290 sh (9,300), 470 (15,250); IR (Nujol) 3480, 1760, 1675, 1630, 1575, 1385, 1310, 1230, 1125, 1045, 1020, 960, 790 cm$^{-1}$; $^1$H NMR (CDCl$_3$) $\delta$ 1.17 (s, 3H, CH$_3$C), 1.26 (d, 3H, CH$_3$C), 1.43 (s, 3H, CH$_3$C), 1.58 (s, 3H, CH$_3$C), 2.12, 2.13 (2s, 6H, CH$_3$CO), 2.26 [s, 6H, (CH$_3$) N], 242-3.77 (m, CH$_2$, CHO, and CHN), 3.20, 3.52 (2s, 9H, 3 CH$_3$O), 5.01-5.31 (m, 3H, H-2', H-4', and H-7), 5.49 (s, 1H, H-1"), 5.84 (d, 1H, H-1'), 7.03 (s, 1H, H-3), 7.48 (s, 1H, H-11); $^{13}$C NMR (CDCl$_3$): $\delta$ 192.1 (C-5), 179.7 (C-12), 170.1, 169.4 (2 CH$_3$CO), 161.7 (C-6), 156.2 (C-4), 147.2 (C-10a), 146.2 (C-1), 135.7 (C-2), 133.7 (C-11a), 130.2 (C-6a), 123.7 (C-3), 120.7 (C-11), 117.4 (C-12a), 115.4 (C-4a), 113.6 (C-5a), 100.1 (C-1"), 92.7 (C-1'), 84.6 (C-4"), 81.2 (C-2"), 77.9 (C-3"), 74.0 (C-5'), 72.4 (C-2', C-7), 70.1 (C-4'), 69.1 (C-9), 67.3 (C-5"), 62.4 (C-3'), 61.4, 58.5, 48.6 (3 CH$_3$O); 45.1 (C-10), 44.0 (C-8), 41.2 [(CH$_3$)$_2$N], 29.3 (C-9 CH$_3$), 23.5 (C-5' CH$_3$), 21.2, 21.1 (2 CH$_3$CO), 18.3 (C-5" CH$_3$), 15.0 (C-3" CH$_3$); mass spectrum, m/e 813.

Anal. Calcd for C$_{41}$H$_{51}$NO$_{16}$: C, 60.58; H, 6.32; N, 1.72. Found: C, 58.46; H, 6.16; N, 1.59.

| | ANTIMICROBIAL SPECTRA | |
|---|---|---|
| | Zone of Inhibition | |
| Test Organism | 2',4'-Di-O—Acetyl-nogalamycin | 2',4'-Di-O—Acetyl-disnogamycin |
| Bacillus subtilis | 29 | 24 |
| B. Subtilis (synthetic) | 26 | 27 |
| B. subtilis, 6033 | 33 | 29 |
| Bacillus cereus | 23 | 15 |
| Sarcina lutea | 25 | 20 |
| S. lutea (sensitive) | 32 | 26 |
| S. lutea, 3383 | 29 | 22 |
| Staphylococcus aureus | 20 | 14 |
| Streptococcus pyogenes | 32 | 28 |
| Clostridium perfringens | 18 | 13 |
| Mycobacterium avium | 26 | 22 |
| Klebsiella pneumoniae | 12 | 0 |
| Escherichia coli | 0 | 0 |
| Proteus vulgaris | 0 | 0 |
| Pseudomonas aeruginosa | 0 | 0 |
| Pseudomonas fluorescens | 0 | 0 |
| Salmonella schottmuelleri | 0 | 0 |
| Salmonella gallinarum | 0 | 0 |
| Rhodopseudomonas sphaeroides | 15 | 10 |

ANTIMICROBIAL SPECTRA

Zone of Inhibition

| Test Organism | 2',4'-Di-O—Acetyl-nogalamycin | 2',4'-Di-O—Acetyl-disnogamycin |
|---|---|---|
| *Bacteroides fragilis* | 32 | 26 |
| *Saccharomyces pasteurianus* | 0 | 0 |
| *Saccharomyces cerevisiae* | 0 | 0 |
| *Penicillium oxalicum* | 0 | 0 |

(6.35 mm discs are dipped into antibiotic solutions of 1 mg per ml of $CHCl_3$)

CHART I

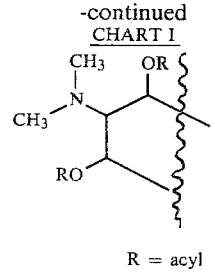

R = acyl

I claim:

1. 2',4'-Diacyl derivative of nogalamycin and its analogs selected from the group consisting of nogalarol, nogalarene, o-methylnogalarol, disnogamycin, nogalamycinic acid, 7-con-O-alkylnogarol, and 7-dis-O-alkylnogarol which retain the dimethylamino moiety, said acyl group consists of hydrocarbon carboxylic acid acyl of from 2 to 18 carbon atoms, inclusive; halo-, nitro-, amino-, cyano-, and lower alkoxy-substituted hydrocarbon carboxylic acid acyl of from 2 to 18 carbon atoms, inclusive.

2. Biologically acceptable acid addition salts of the compound of claim 1.

3. 2',4'-Di-O-acetylnogalamycin, a compound according to claim 1.

4. 2',4'-Di-O-acetyldisnogamycin.

5. A process for preparing regioselective acylates at the 2',4' positions of nogalamycin and its analogs selected from the group consisting of nogalarol, nogalarene, o-methylnogalarol, disnogamycin, nogalamycinic acid, 7-con-O-alkylnogarol, and 7-dis-O-alkylnogarol which retain the dimethylamino moiety which comprises (a) reacting a mixture of nogalamycin or any of its analogs selected from the group consisting of nogalarol, nogalarene, o-methylnogalarol, disnogamycin, nogalamycinic acid, 7-con-O-alkylnogarol, and 7-dis-O-alkylnogarol which retain the dimethylamino moiety with an acid halide and methanol, and (b) recovering the desired acylated product from the completed reaction.

6. A process, according to claim 5, wherein nogalamycin, methanol, and acetic anhydride are reacted, and 2',4'-di-O-acetylnogalamycin is recovered from the completed reaction.

7. A process, according to claim 5, wherein disnogamycin, methanol, and acetic anhydride are reacted, and 2',4'-di-O-acetyldisnogamycin is recovered from the completed reaction.

* * * * *